US010729866B2

(12) United States Patent
Cook

(10) Patent No.: US 10,729,866 B2
(45) Date of Patent: Aug. 4, 2020

(54) LARYNGEAL MASK WITH GASTRIC DRAINAGE FEATURE IN SEALING RING

(71) Applicant: Cookgas, LLC, St. Louis, MO (US)

(72) Inventor: Daniel J. Cook, St. Louis, MO (US)

(73) Assignee: COOKGAS, LLC, St. Louis, MO (US)

( * ) Notice: Subject to any disclaimer, the term of this patent is extended or adjusted under 35 U.S.C. 154(b) by 500 days.

(21) Appl. No.: 15/432,399

(22) Filed: Feb. 14, 2017

(65) Prior Publication Data

US 2018/0228991 A1 Aug. 16, 2018

(51) Int. Cl.
*A61M 16/04* (2006.01)
*A61M 39/08* (2006.01)

(52) U.S. Cl.
CPC .... *A61M 16/0463* (2013.01); *A61M 16/0434* (2013.01); *A61M 39/08* (2013.01)

(58) Field of Classification Search
CPC ...................... A61M 16/0463; A61M 16/0434
See application file for complete search history.

(56) References Cited

U.S. PATENT DOCUMENTS

| | | | |
|---|---|---|---|
| 5,355,879 A * | 10/1994 | Brain | A61M 16/04 128/207.15 |
| 5,878,745 A | 3/1999 | Brain | |
| 6,631,720 B1 | 10/2003 | Brain | |
| 7,004,169 B2 | 2/2006 | Brain | |
| RE39,938 E | 12/2007 | Brain | |
| 8,449,713 B2 | 5/2013 | Brain | |
| 9,463,296 B2 | 10/2016 | Stix | |
| 2004/0089307 A1 | 5/2004 | Brain | |
| 2008/0142017 A1 | 6/2008 | Brain | |
| 2008/0276936 A1* | 11/2008 | Cook | A61M 16/0057 128/204.18 |
| 2014/0000624 A1 | 1/2014 | Miller | |
| 2015/0128946 A1* | 5/2015 | Stix | A61M 16/0415 128/204.18 |

OTHER PUBLICATIONS

Brimacombe, "Laryngeal mask anesthesia: Principles and practice, 2nd edition," Saunders, Philadelphia. Excerpt Ch. 1, "History," pp. 29-31 (2005).

* cited by examiner

*Primary Examiner* — Manuel A Mendez
*Assistant Examiner* — Tasnim Mehjabin Ahmed
(74) *Attorney, Agent, or Firm* — Thompson Coburn LLP

(57) ABSTRACT

An airway has a ventilation tube with a mask attached to its distal end. The mask has a base and a sealing ring surrounding the base. The sealing ring has an exterior side surface extending around the base, an upper surface extending from the exterior side surface toward a center of the base, and an inner surface extending from the upper surface toward the center of the base. The exterior surface, upper surface, and inner surface define an inner volume within the sealing ring. The sealing ring and base define a cavity in the mask. An evacuation tube is attached to a proximal end of the mask and extends through the inner volume of the sealing ring to a distal end of the mask where it forms an opening on the mask distal end on the sealing ring exterior side surface.

20 Claims, 7 Drawing Sheets

LARYNGEAL MASK WITH GASTRIC DRAINAGE FEATURE IN SEALING RING

BACKGROUND AND SUMMARY

This disclosure relates generally to a laryngeal mask with a gastric drainage feature. More in particular, the gastric drainage feature is directed from the airway and proximal end of the mask through the sealing ring to the distal end of the mask to provide clearance in the cavity of the mask for endotracheal tubes and other instruments.

DETAILED DESCRIPTION

Figure 1:
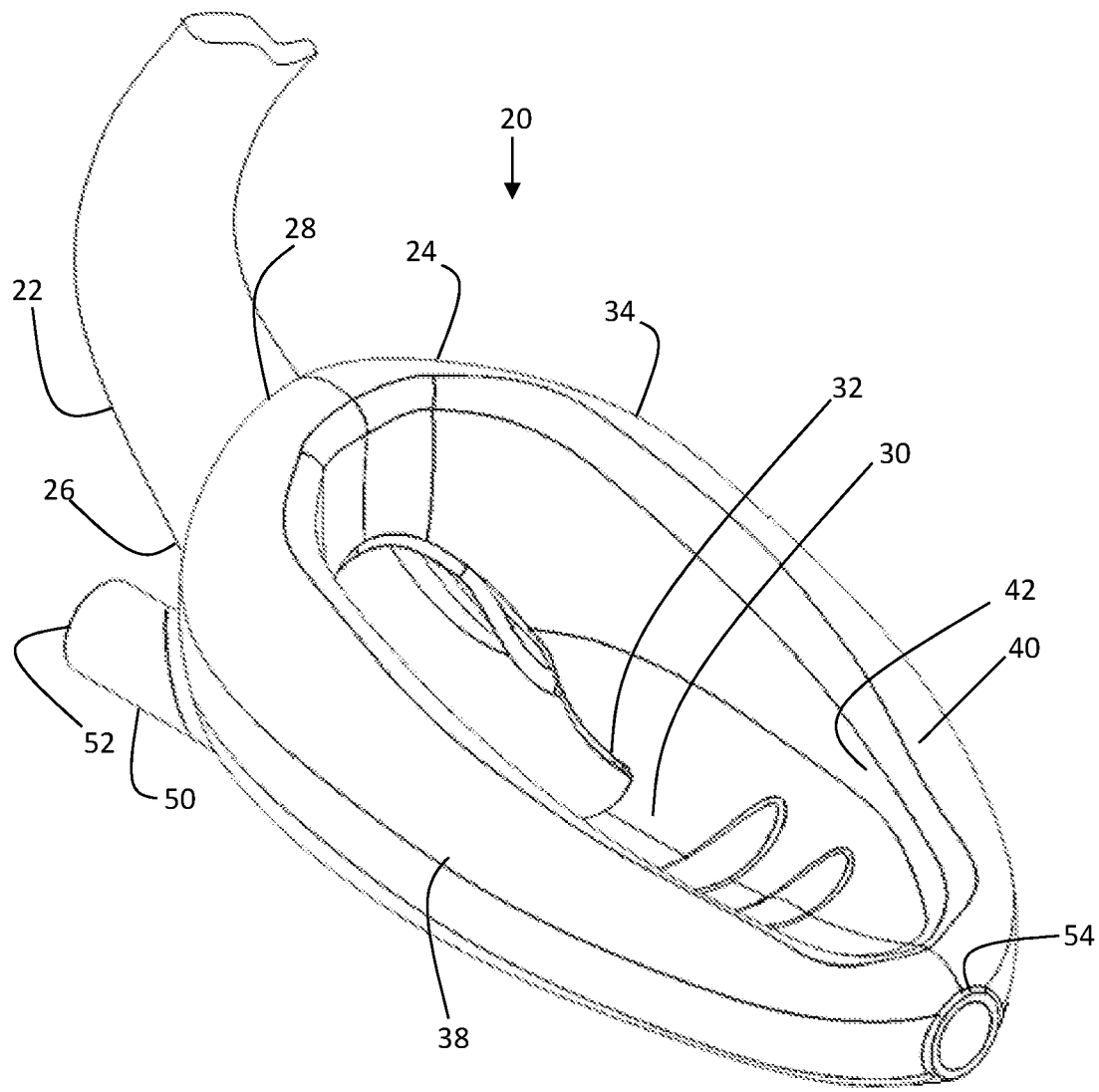
FIG. 1 is a perspective view of an exemplary airway device having at its distal end a gastric-drainage feature.
Figure 2:
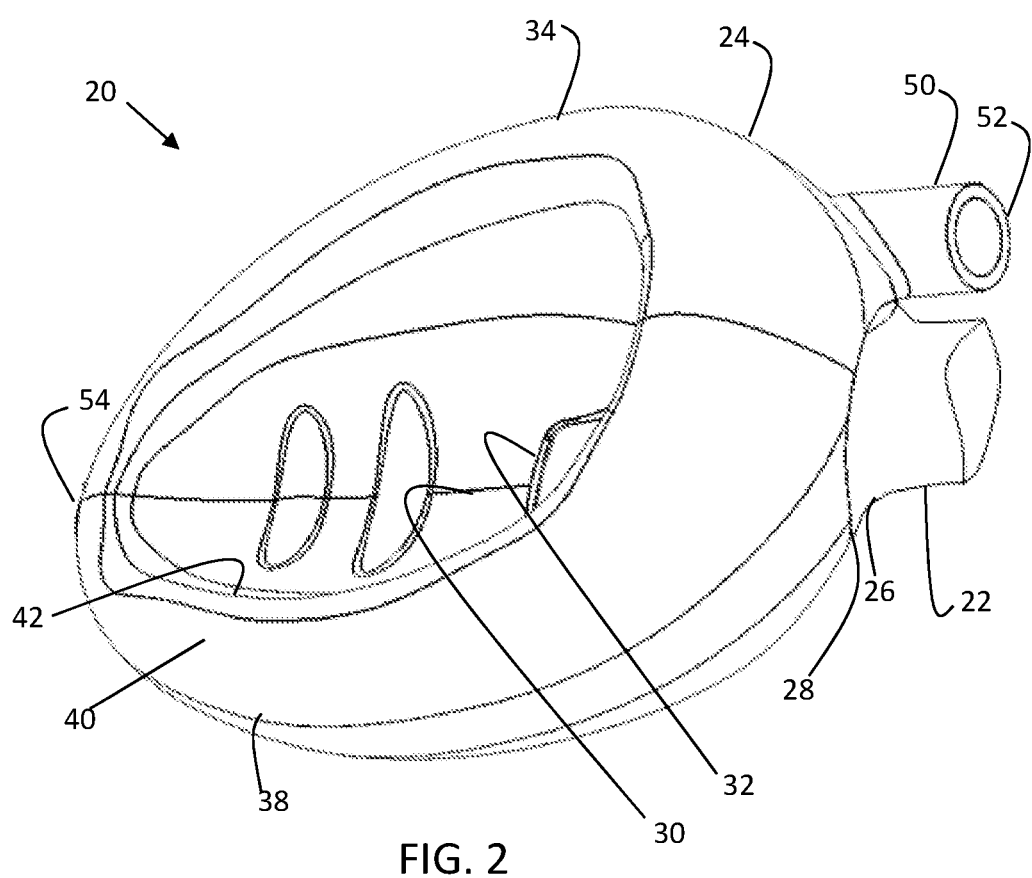
FIG. 2 is an alternative perspective view of the mask of FIG. 1.
Figure 3:
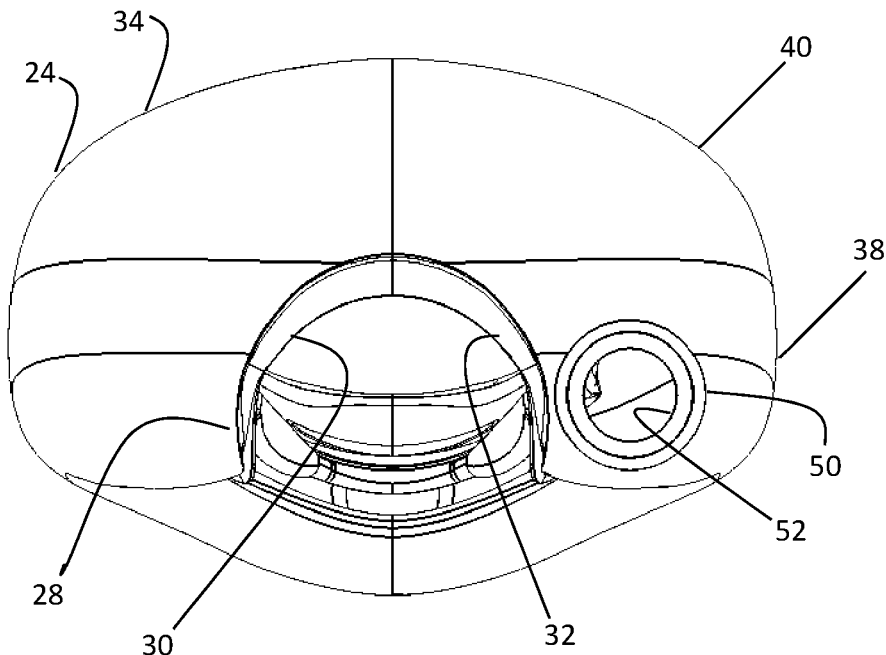
FIG. 3 is a proximal end view of the mask of FIG. 1.
Figure 4:
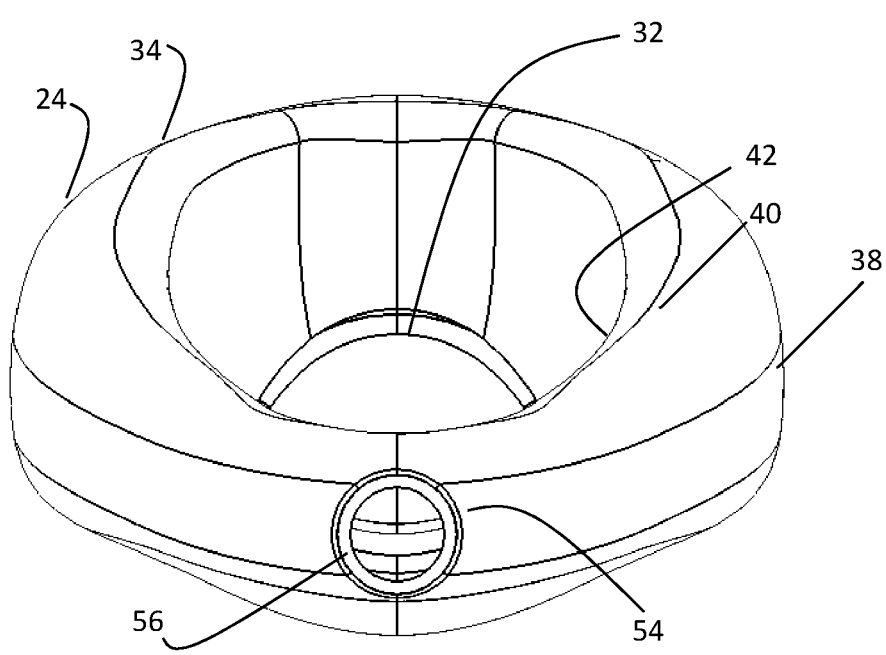
FIG. 4 is a distal end view of the mask of FIG. 1.
Figure 5:
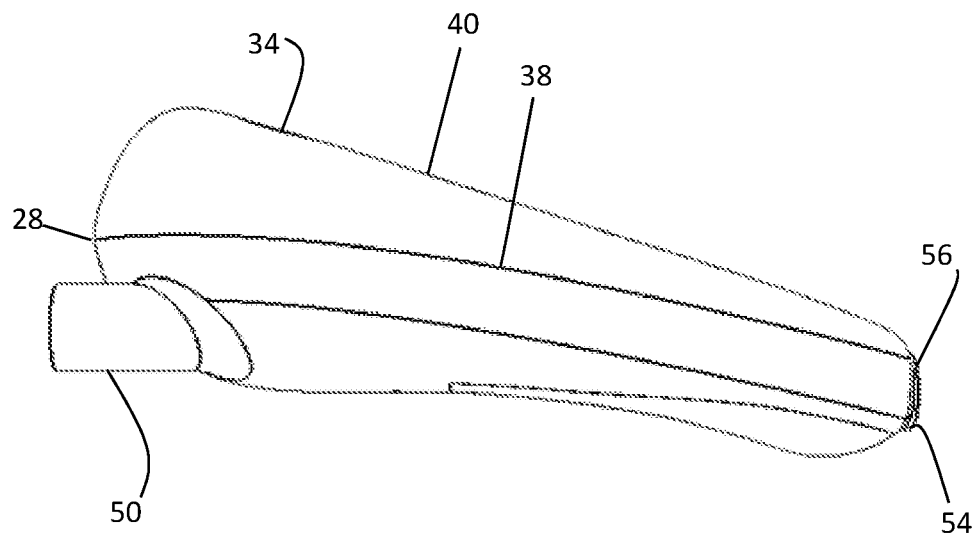
FIG. 5 is a side elevational view of the mask of FIG. 1.
Figure 6:
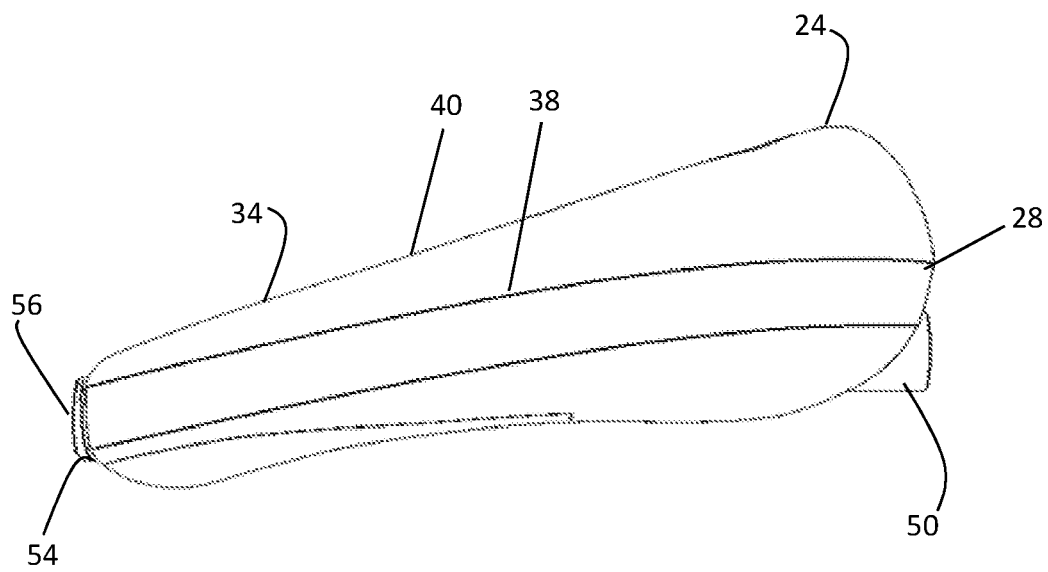
FIG. 6 is a side elevational view of the mask opposite the view of FIG. 5.
Figure 7:
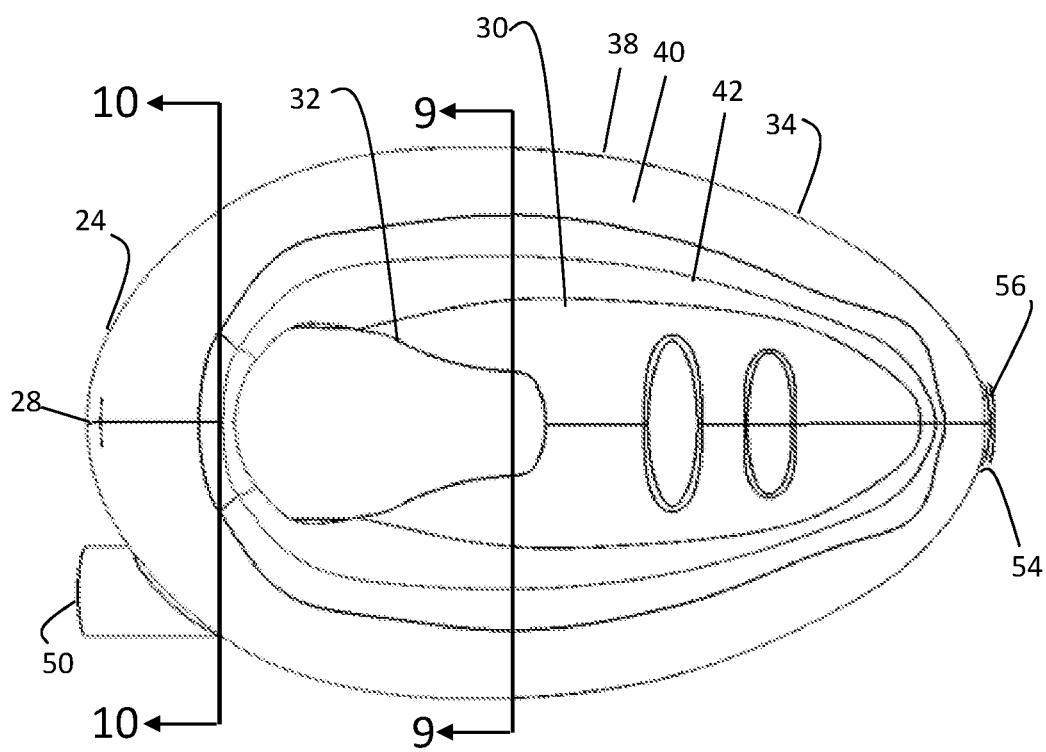
FIG. 7 is a plan view of the mask of FIG. 1.
Figure 8:
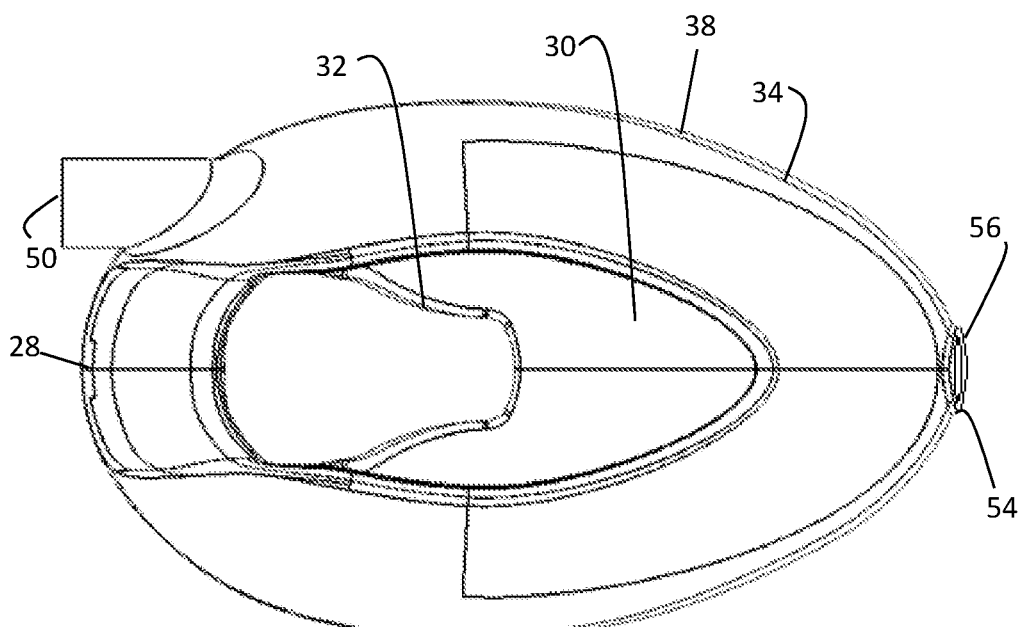
FIG. 8 is a bottom view of the mask of FIG. 1.
Figure 9:
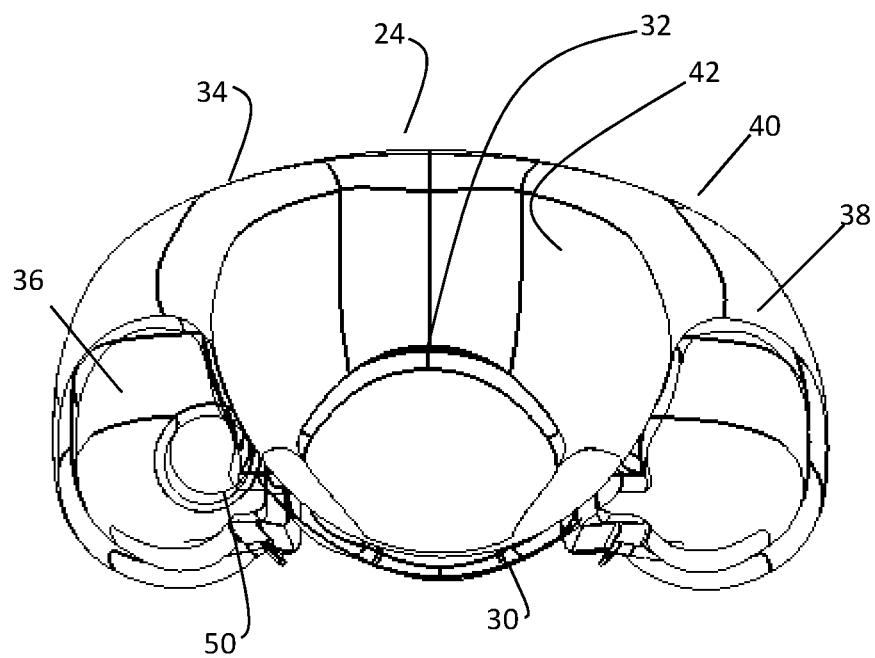
FIG. 9 is a cross sectional end view of the mask along lines 9-9 of FIG. 7.
Figure 10:
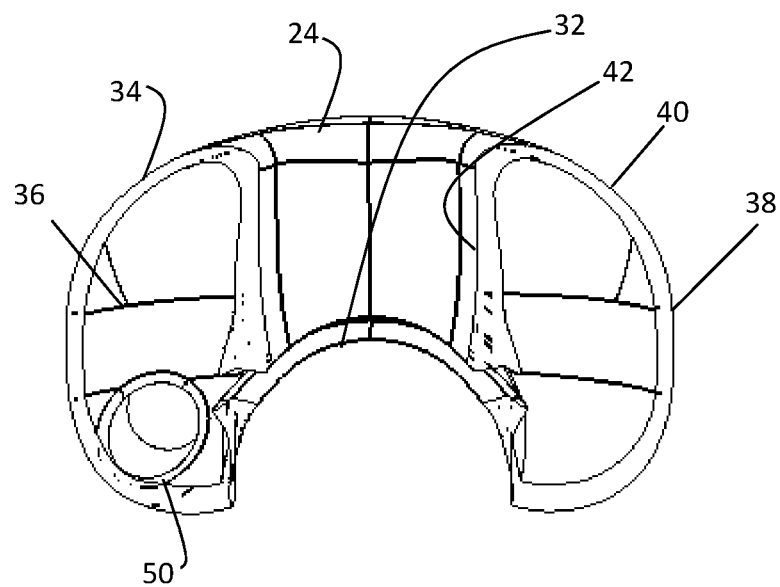
FIG. 10 is a cross sectional end view of the mask along lines 10-10 of FIG. 7.
Figure 11:
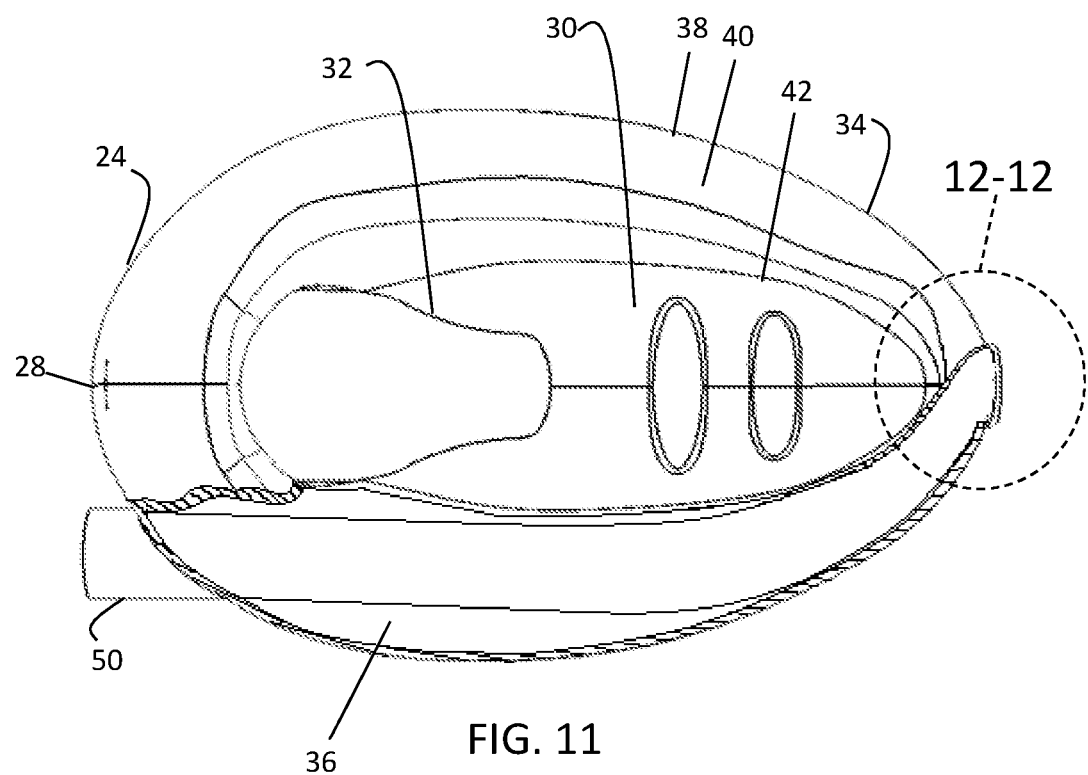
FIG. 11 is a plan view of the mask with a portion of the sealing ring removed to provide additional detail of the gastric-drainage feature.

Referring embodiments of FIGS. 1 to 11, the laryngeal airway system 20 comprises a ventilation tube 22 and a mask 24 configured to be installed through the mouth of a patient. The airway system 20 may be generally as described in any of U.S. Pat. Nos. 5,937,860, 6,422,239, 7,934,502, 8,622,060, 8,978,658, and 9,320,864, the disclosures of which are incorporated by reference herein, and therefore not described in detail herein. The ventilation tube 22 has opposite distal 26 and proximal ends (not shown) with a gently curving length extending therebetween. The ventilation tube diameter and curvature is sufficient to permit the passage of endo-tracheal tubes, and related medical instruments therethrough. The ventilation tube proximal end may be connected to a ventilation apparatus. The ventilation tube distal end 26 is secured to the proximal end 28 of the mask. The mask 22 has a relatively stiff base 30 having an opening 32 at which the ventilation tube 22 is connected and can establish a ventilation passage via the patient's mouth and throat, and past the epiglottis to the larynx. The base may have a recessed front and may be notched to securely surround the trachea after inflation, preventing lateral movement of the mask. The mask has a sealing ring 34 along an outer periphery of the base which together with the base defines a cavity within the mask such that generally speaking the mask is dome-shaped with its concave side and sealing ring defining a generally elliptical arrangement facing and sealing the laryngeal inlet, and its convex side facing the back wall of the pharynx when in use with a patient. The base 30 may be made from suitable elastomer such as silicone rubber and is relatively stiff. The sealing ring 34 may also be made of a silicone rubber, although preferably relatively soft and flexible compared to base. In one embodiment, an externally accessible tube (not shown) is the means of supplying air to and relieving air from the sealing ring, for instance, as described in U.S. Pat. Nos. 5,937,860 and 6,422,239. In other embodiments, the primary airway may provide the means to supply air to and relieve air from the sealing ring, for instance, as described in U.S. Pat. Nos. 7,934,502, 8,622,060, 8,978,658, and 9,320,864.

The sealing ring 34 generally comprises a ring shape which is hollow and forms a generally hollow inner volume 36. Generally, the sealing ring 34 has an exterior side 38, an upper surface 40 which bends generally inward toward the center of the base from the exterior side. The upper surface 40 may then be connected to an inner side 42 which is directed back down and toward the interior surface of the base. Depending on embodiment, the inner side 42 may attach to the base so as to provide the sealing ring with the tube-like structure or may not providing a more channel-like structure with the inner side extending a predetermined distance toward the base before ending, for instance, with the inner side being suspended above the base, completely around the sealing ring or in an interrupted pattern around the sealing ring. In one embodiment, in order to provide air introduced into the airway for use by the patient and for use to pressurize the sealing ring, a fluid communication port may be provided to allow for fluid (particularly gas in the form of ventilated air) to pass from the air path to the interior of the sealing ring. This fluid communication port may be located anywhere in the air path providing access to the inner volume of the sealing ring. The port may be located near the distal end of the respiratory tube providing fluid flow from the respiratory tube to the inner volume of the sealing ring. The port may comprise holes located in the interior surface of the sealing ring providing fluid flow from the cavity to the inner volume of the sealing ring. The port may be an elongated generally continuous slit in the interior surface which circumscribes the cavity.

The mask has an evacuation tube 50 that allows for the extraction and external removal of gastric-discharge products from the esophagus. The evacuation tube 50 may be separate and apart from the ventilation tube 22 (and as the case may be, the sealing ring inflation source), and is connected to the mask 24 at an evacuation discharge opening 52 extending through the sealing ring 34 adjacent the proximal end 28 of the mask. The evacuation tube 50 may be integral with the ventilation tube 22 (a separate tube but side-by-side with the ventilation tube) until just before the proximal end 28 of the mask, where the ventilation tube may be directed to the base 30 and the evacuation tube 50 toward the sealing ring 34 on a lateral side of the ventilation of tube. The evacuation tube 50 may be generally adjacent to the ventilation tube on the proximal end of the mask. While the drawings show the evacuation tube 50 on the right lateral side of the mask (with reference to FIG. 1, FIG. 3, and FIG. 7), the evacuation tube may also be arranged on the opposite side of the ventilation tube. The position of entry of the evacuation tube 50 into the sealing ring 34 and the mask 24 allows the evacuation tube to have a seamless transition into the inner volume 36 defined by the sealing ring. The evacuation tube 50 may enter into the sealing ring 34 at a position ranging from at the center of the portion of the sealing ring at the proximal end 28 of the of the mask to a position adjacent to the base 30 at the proximal end of the of the mask. The discharge opening 52 may be formed in the sealing ring 34 at the proximal end of the mask and the evacuation tube may connect to the discharge opening or pass through the discharge opening depending upon the desired configuration of the discharge opening.

Figure 12:
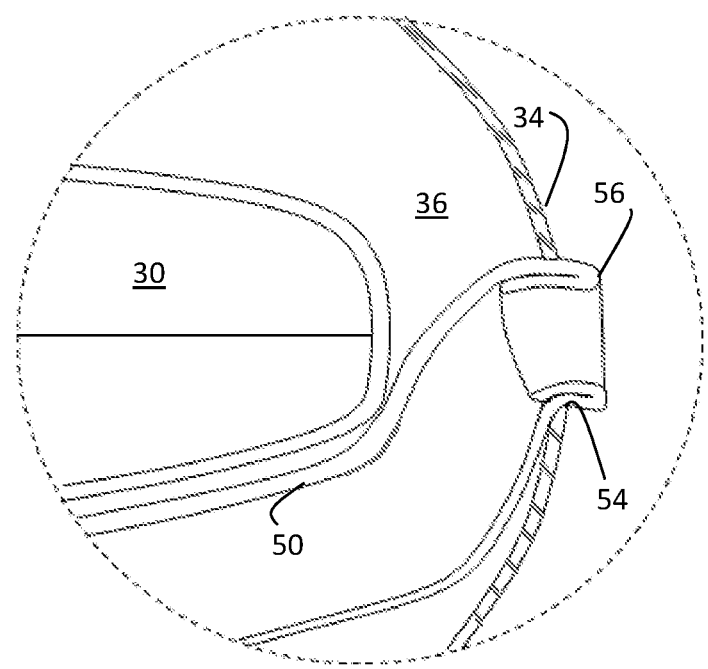
FIG. 12 is an enlarged view of one embodiment of a distal end of the mask taken from detail area 12-12 of FIG. 11.

Once in the inner volume 36 defined by the sealing ring 34, the evacuation tube 50 may generally follow the contour of the outer periphery of the base 30 within the hollow interior of the sealing ring. The evacuation tube 50 may be separated from but contained within the sealing ring 34. For instance, the evacuation tube 50 may not be connected to the sealing ring 34 other than at the proximal end of the mask where the evacuation tube is connected to the mask at the evacuation discharge opening 52, and at a distal end 54 of the mask where the evacuation tube forms the evacuation inlet opening 56 on the exterior side surfaces of the sealing ring. Likewise, the evacuation tube may not be connected to the base. The evacuation tube 50 may be positioned in the inner volume 36 of the sealing ring in a manner to allow the sealing ring to perform its sealing function. For instance, the evacuation tube 50 may be centered in the sealing ring 34 to allow unobstructed inflation and deflation of the sealing ring and to allow the sealing ring to easily conform to the patient's laryngeal opening. As the evacuation tube 50 passes through the inner volume 36 of sealing ring 34 toward the distal end 54 of the mask, the evacuation tube may be aligned with the centerline of the mask and extend through the sealing ring to the exterior of the mask and form the evacuation inlet opening 56. The evacuation tube 50 may form the evacuation inlet opening 56 or may pass through the evacuation inlet opening. At the distal end 54 of the mask, the evacuation tube 56 may be integrally formed with the relatively soft material of the sealing ring 34. At the distal end of the mask 54, the evacuation tube 50 may be pulled back or double within itself or inner volume (see FIG. 12) to form a suitable smooth transition and surface for the exterior of the mask. The evacuation tube 50 may be a separate tubular member inserted in molding equipment when molding the mask in accordance with any of the methods described in U.S. Pat. Nos. 5,937,860, 6,422,239, 7,934,502, 8,622,060, 8,978,658, and 9,320,864. The evacuation tube 50 may be adhered to or molded with the mask. The evacuation tube 50 does not communicate with the inner volume 36 of the sealing ring 34 and may be arranged so as to allow free communication between both halves of the hollow interior of the sealing ring. Thus, the evacuation tube 50 may be arranged in the inner volume of the sealing ring to permit a flow of air around the sealing ring when the sealing ring is inflated. While the drawings show the evacuation tube as a separate member within the inner volume of the sealing ring, the evacuation tube may be a passageway monolithically or integrally formed in inner volume of the sealing ring.

With the evacuation tube extending through the hollow interior of the sealing ring as it passes from the proximal end of the mask to the distal end of the mask, the cavity remains unobstructed and the area of the airway remains as large as possible to allow endotracheal tubes and other instruments to be passed through the mask to the patient's larynx. The evacuation tube may be sized and formed from a material that allows it to readily conform to the contour to the outer periphery of the base within the hollow interior of the sealing ring, including the portion of the evacuation tube that passes through the sealing ring at the distal end of the mask. One may attach the proximal end of the ventilation tube to a ventilation apparatus and force air into ventilation tube to provide air to the patient while draining fluid from the patient through the evacuation tube, as necessary. In forcing air into the ventilation tube to provide air to the patient, one may inflate the sealing ring.

In view of the foregoing, it will be seen that the several advantages are achieved and attained. The embodiments were chosen and described in order to best explain the principles and their practical application to thereby enable others skilled in the art to best utilize the various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A supraglottic airway comprising;
   a ventilation tube having a distal end, a proximal end, and a length therebetween, the ventilation tube having a hollow interior; and
   a mask attached to the distal end of the ventilation tube at a proximal end of the mask, the mask comprising a base and a sealing ring surrounding the base, the sealing ring having an exterior side surface extending substantially around the base, the sealing ring defining a posterior side of the mask at the proximal end of the mask, the sealing ring having an upper surface extending from the exterior side surface toward a center of the base, the sealing ring having an inner surface extending from the upper surface toward the center of the base, the exterior surface, upper surface, and inner surface defining an inner volume within the sealing ring, the sealing ring and base defining a cavity in the mask; and
   an evacuation tube attached to the proximal end of the mask, the evacuation tube entering into the inner volume of the sealing ring: (i) at the proximal end of the mask on the posterior side of the mask and (ii) with a posterior side of the evacuation tube posterior relative to a vertical center of the base, the evacuation tube extending through the inner volume of the sealing ring to a distal end of the mask and communicating with an opening at the distal end of the mask at the medial line of the mask on the exterior side surface of the sealing ring.

2. The airway of claim 1 wherein the hollow interior of the ventilation tube is in fluid communication with the cavity, the hollow interior of the ventilation tube and the cavity jointly define an air path; and the inner volume of the sealing ring is capable of fluid communication with the air path.

3. The airway of claim 1 wherein the evacuation tube is not connected to the sealing ring other than at the proximal end of the mask where the evacuation tube is connected to the mask and at the distal end of the mask where the evacuation tube forms the opening on the distal end of the mask on the exterior side surface of the sealing ring.

4. The airway of claim 1 wherein the evacuation tube is not connected to the base.

5. The airway of claim 1 wherein the evacuation tube is arranged in the inner volume of the sealing ring to permit a flow of air around the evacuation tube when the sealing ring is inflated.

6. The airway of claim 1 wherein the evacuation tube is an insert molded with the mask.

7. The airway of claim 1 wherein the evacuation tube is doubled over within an inner volume of the evacuation tube in forming the opening on the distal end of the mask on the exterior side surface of the sealing ring.

8. A method of providing an artificial airway to a human comprising:
   placing in the throat of a human, a supraglottic airway comprising;
      a ventilation tube having a distal end, a proximal end, and a length therebetween, said ventilation tube defining a hollow interior;
      a base and a sealing ring surrounding the base, the sealing ring having an exterior side surface extending substantially around the base, the sealing ring defining a posterior side of the mask at the proximal end of the mask, the sealing ring having an upper surface extending from the exterior side surface toward a center of the base, the sealing ring having an inner surface extending from the upper surface, together the exterior side surface, the upper surface, and the inner surface defining an inner volume within the sealing ring with the sealing ring and base forming a cavity within the mask; and
      an evacuation tube attached to the mask, the evacuation tube entering into the inner volume of the sealing ring: (i) at the proximal end of the mask on a posterior side of the mask and (ii) with a majority of the evacuation tube disposed posterior relative to a vertical centerline of the base, the evacuation tube extending through the hollow interior of the sealing ring to a distal end of the mask and communicating with an opening at the distal end of the mask at the medial line of the mask on the exterior side surface of the sealing ring;
   attaching the proximal end of the ventilation tube to a ventilation apparatus; and
   forcing air into ventilation tube to provide air to the patient; and
   draining fluid from the patient through the evacuation tube.

9. The method of claim 8 wherein the step of forcing air into the ventilation tube alters the pressure in the inner volume of the sealing ring.

10. A laryngeal mask comprising:
    a base and a sealing ring extending around the base, the sealing ring being configured to seal around a circumference of a patient's laryngeal opening when the mask is installed in the patient's oropharynx, the base being configured to prevent lateral movement of the laryngeal mask when positioned in the patient's oropharynx, the sealing ring extending substantially around the base and defining a posterior side of the mask at the proximal end of the mask, the sealing ring and base defining a cavity in the mask; and
    a flexible ventilation tube having a distal end connected to a proximal edge of the base; and
    an evacuation inlet opening formed in the sealing ring at a distal end of the mask at a medial line of the mask, and an evacuation discharge opening formed in the sealing ring at a proximal end of the mask on a posterior side of the mask, the evacuation discharge opening having a center posterior relative to a vertical center of the base, the evacuation inlet opening communicating with an evacuation passage disposed in the inner volume of the sealing ring, the evacuation passage extending from the distal end of the mask at the evacuation inlet opening to the proximal end of the mask at the evacuation discharge opening.

11. The airway of claim 10 wherein the hollow interior of the ventilation tube is in fluid communication with the cavity, the hollow interior of the ventilation tube and the cavity jointly define an air path; and the inner volume of the sealing ring is capable of fluid communication with the air path.

12. The airway of claim 10 wherein an evacuation tube forms the evacuation passage.

13. The airway of claim 12 wherein the evacuation tube forms the evacuation inlet opening.

14. The airway of claim 13 wherein the evacuation tube passes through the evacuation discharge opening.

15. The airway of claim 14 wherein the evacuation tube is not connected to the sealing ring other than at the evacuation inlet opening and at the evacuation discharge opening.

16. The airway of claim 12 wherein the evacuation tube is not connected to the base.

17. The airway of claim 12 wherein the evacuation tube is an insert molded with the mask.

18. The airway of claim 12 wherein the evacuation tube is doubled over within its inner volume in forming the evacuation inlet.

19. The airway of claim 10 wherein the evacuation passage is configured to permit a flow of air around the evacuation tube when the sealing ring is inflated.

20. The airway of claim 10 wherein the evacuation discharge opening is adjacent to a connection of the ventilation tube to the mask.

* * * * *